United States Patent [19]

Zanker

[11] 4,069,238
[45] Jan. 17, 1978

[54] MANUFACTURE OF ALIPHATIC ISOCYANATES

[75] Inventor: Fritz Zanker, Worms, Germany

[73] Assignee: BASF Aktiengesellschaft, Ludwigshafen, Germany

[21] Appl. No.: 649,740

[22] Filed: Jan. 16, 1976

[30] Foreign Application Priority Data

Jan. 28, 1975 Germany .............................. 2503270

[51] Int. Cl.$^2$ ............................................ C07C 118/00
[52] U.S. Cl. .................................................. 260/453 P
[58] Field of Search ...................... 260/453 P, 453 PH

[56] References Cited
U.S. PATENT DOCUMENTS 3,465,023  9/1969  Ramal ................................. 260/453
3,969,389  7/1976  Urbach et al. ................... 260/453 P
3,991,094  11/1976  Zanker ............................. 260/453 P

FOREIGN PATENT DOCUMENTS 2,411,442  10/1975  Germany.

Primary Examiner—Dolph H. Torrence
Attorney, Agent, or Firm—Keil, Thompson & Shurtleff

[57] ABSTRACT

A process for the manufacture of aliphatic isocyanates by thermal decomposition of aliphatic carbamic acid halides. The decomposition is carried out in stages and the hydrogen halide liberated is expelled, in the first stage, without passing inert gas through the reaction mixture, while in the second stage it is expelled while passing an inert gas, which is recycled, through the reaction mixture.

7 Claims, No Drawings

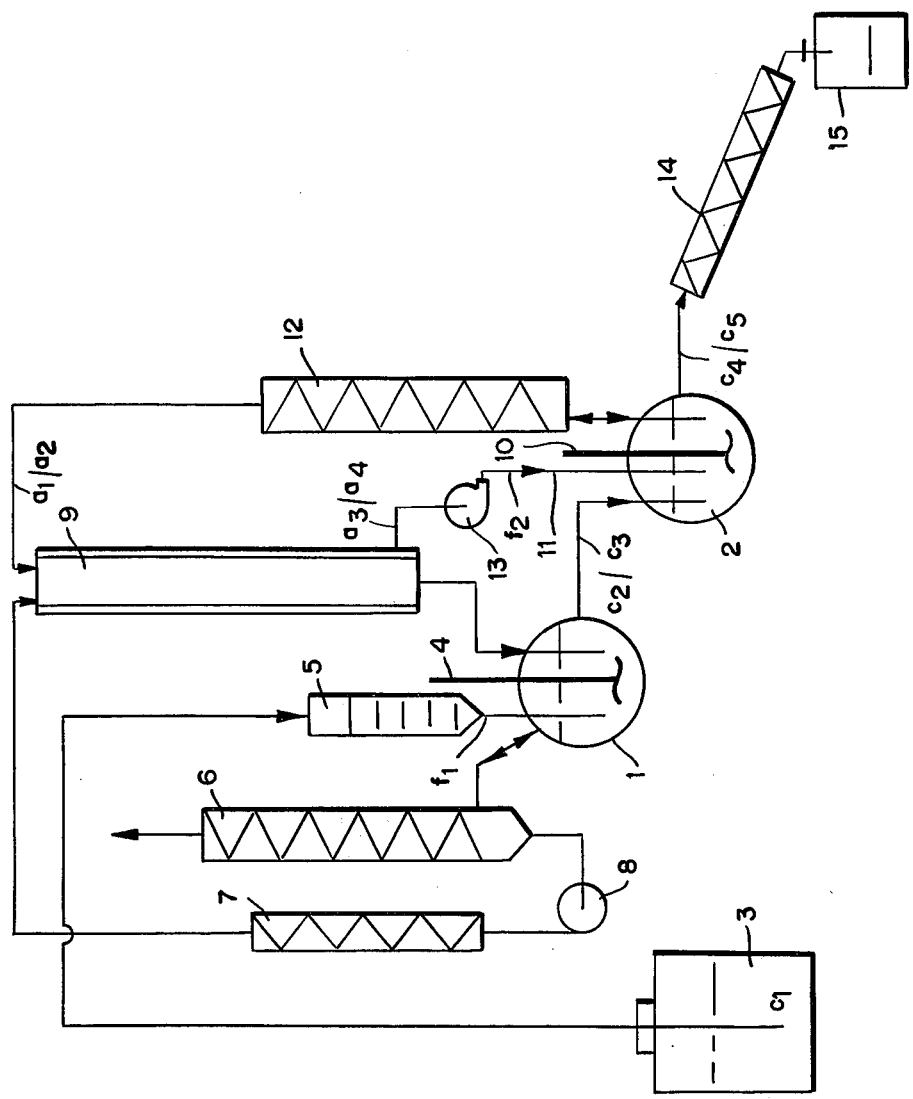

MANUFACTURE OF ALIPHATIC ISOCYANATES

The present invention relates to a process for the manufacture of aliphatic isocyanates by partial thermal decomposition of aliphatic carbamic acid halides in a first reaction vessel, further thermal decomposition, whilst passing an inert gas through the reaction mixture, in a second reaction vessel, subsequent removal of hydrogen halide from the inert gas by absorption in a mixture containing isocyanate, so as to give carbamic acid halide, at below the decomposition temperature, introduction of this absorption liquid, containing the carbamic acid halide, into the first reaction vessel, and recycling of the purified inert gas into the second reaction vessel.

The manufacture of isocyanates by thermal decomposition of carbamic acid halides in the presence of inert organic solvents has been disclosed. The reaction can be represented by the following equation:

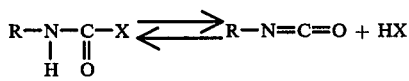

To prevent occurrence of the reverse reaction, the hydrogen halide must be removed from the equilibrium.

If the decomposition is carried out in the presence of organic bases, eg. tertiary amines or N,N-dialkylcarboxylic acid amides (German Published Application No. 1,593,554), or of aqueous solutions or suspensions of acid acceptors, eg. alkali metal hydroxides, alkaline earth metal hydroxides, alkali metal carbonates, alkaline earth metal carbonates, alkali metal bicarbonates, trialkylamines, pyridine and N-methylpiperidine (British Pat. No. 1,208,862) the hydrogen halide formed during the reaction can be chemically bonded to these compounds.

The above processes have the disadvantage that the isocyanates are produced in a medium in which they are prone to decompose. Houben-Weyl, Methoden der organischen Chemie, Volume 8, page 136, Georg Thieme-Verlag, 4th Edition (1952), discloses the isocyanates dimerize in the presence of tertiary amines. They are also extremely unstable to aqueous alkali and are largely converted to carbamates or carbamic acids even if only stoichiometric amounts of aqueous alkali are used.

An article in Annalen der Chemie 562 (1949), 75–109 discloses the thermal decomposition of N-phenyl-carbamic acid chloride and points out that the isocyanates can only be isolated if the hydrogen chloride produced is bonded by reaction with chemical reagents, eg. calcium oxide. In this system, side-reactions, eg. the formation of polymeric isocyanates, occasionally occur. It is alleged in the same publication that the decomposition yields isocyanates only in the case of aromatic carbamic acid chlorides, but not in the case aliphatic carbamic acid chlorides.

In contrast, German Pat. No. 1,193,034 proposes that the hydrogen chloride produced in the thermal decomposition of alkylcarbamic acid chlorides be removed from the reaction chamber through a reflux condenser and at the same time the isocyanate produced be distilled off through a separate column.

A process has also been proposed, in German Published Application No. 2,411,442, wherein the thermal decomposition to give aliphatic isocyanates is carried out whilst passing an inert gas through the reaction mixture and the hydrogen halide produced is removed from the reaction chamber by this inert gas. Solvent, isocyanate and carbamic acid halide entrained by the gases may, eg., be washed out from them with solvents and subjected to renewed thermal decomposition. However, the inert gas treated in this way still contains hydrogen halide, and yet the economics of the entire process depend on the availability of an industrially acceptable method of purifying this gas and subsequently re-using it. It is necessary to free the inert gas from hydrogen halide because the concentration of the latter in the former would progressively rise as the inert gas was recycled. In line with this rise in the hydrogen halide partial pressure in the gas space, the concentration of hydrogen halide in the solution containing carbamic acid halide and isocyanate would increase, and would favor the re-formation of carbamic acid halide from isocyanate and hydrogen halide. Anything approximating complete thermal elimination of hydrogen halide from alkylcarbamic acid halides would prove impossible if the inert gas recycled was laden with hydrogen halide.

For this reason it is necessary to absorb the hydrogen halide, entrained with the inert gas, in water to give hydrochloric acid and then recycle the inert gas; this, however, demands thorough drying of the inert gas after it has been freed from hydrogen halide and before recycling, since both alkylcarbamic acid halides and alkyl isocyanates are extremely sensitive to moisture. It is, specifically, this drying process which makes the recovery of the inert gas, and hence the entire process, extremely expensive.

I have found that aliphatic isocyanates of the formula

    I where R is an aliphatic radical of 1 to 10 carbon atoms, are obtained in an advantageous manner by thermal decomposition of aliphatic carbamic acid halides of the formula

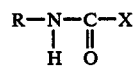    II where R has the above meaning and X is halogen, in the presence of an inert organic solvent, if the thermal decomposition is carried out in the presence of the inert organic solvent in a first reaction vessel for not longer than is required to set up the equilibrium, the hydrogen halide eliminated during this stage is removed through a reflux condenser, the carbamic acid halide/isocyanate mixture obtained in the first reaction vessel is transferred into a second reaction vessel, the thermal decomposition of the remaining carbamic acid halide is continued therein whilst passing inert gas through the mixture, the hydrogen halide entrained with the inert gas is reacted with isocyanate, below the decomposition temperature, to give carbamic acid halide, the mixture containing carbamic acid halide, thus obtained, is introduced into the first reaction vessel, and the purified inert gas is recycled to the second reaction vessel.

The advantages of the process of the invention over the cited processes of the prior art are that the inert gas passed into the second reaction vessel is recycled and that the process is free from the costs incurred either by using large quantities of fresh inert gas or by drying processes which are necessary if the hydrogen halide is removed by absorption in water.

The total amount of hydrogen halide liberated during the reaction is expelled from the first reaction vessel without passing inert gas through the mixture, so that the trapping of the hydrogen halide, eg. by absorption in water, which is conventionally carried out in columns, entails less expenditure on apparatus.

Preferred starting materials II, and accordingly, preferred end products I are those where R is alkyl of 1 to 10 carbon atoms, preferably of 1 to 4 carbon atoms and especially of 2 or 3 carbon atoms, alkenyl of 2 to 6 carbon atoms or alkynyl of 2 to 6 carbon atoms and X is bromine or preferably chlorine. The above radicals can further be substituted by groups and/or atoms which are inert under the reaction conditions, eg. alkyl, alkoxy or alkylmercapto each of 1 to 5 carbon atoms, or chlorine atoms.

Examples of suitable starting materials II are methyl-, ethyl-, n-propyl-, i-propyl-, n-butyl-, i-butyl-, sec.-butyl-, t-butyl-, 2-methylbutyl-1-, 3-methylbutyl-1-, 2-methylbutyl-2-, 3-methylbutyl-2-, pentyl-1-, pentyl-2-, pentyl-3-, neo-pentyl-, n-hexyl-, n-octyl-, allyl-, 3,3-dimethylallyl-3-, 3-methyl-3-ethyl-allyl-3-, 1-butynyl-3-, 3-methyl-1-butynyl-3-, 3-methyl-1-pentynyl-3-, 2-methoxyethyl-, 2-ethoxyethyl-, 3-methoxypropyl-, 3-ethoxypropyl-, 1-methoxy-butyl-2-, 1-n-propoxy-propyl-2-, methoxy-t-butyl-, ethoxy-t-butyl-, methylmercaptopropyl- and ethylmercaptopropyl-carbamic acid chloride and corresponding carbamic acid bromides. Ethylcarbamic acid chloride, n-propyl-carbamic acid chloride and isopropylcarbamic acid chloride are preferred.

The decomposition is in general carried out at from +30° to 180° C, preferably at from 45° to 140° and especially at from 70° to 115° C, suitably under reflux, at the boiling point of the decomposition mixture of starting material II and solvent, under atmospheric or superatmospheric pressure, continuously or batchwise.

The solvents used are organic solvents which are inert under the reaction conditions and preferably those which are good solvents for the starting material II but non-solvents or poor solvents for the hydrogen halide. Appropriate solvents have boiling points of not less than 60° C. Examples of suitable solvents are aromatic hydrocarbons, eg. benzene, toluene, ethylbenzene, o-, m- and p-xylene, isopropylbenzene, o-, m- and p-cymene, methylnaphthalene, halohydrocarbons, especially chlorohydrocarbons, eg. tetrachloroethylene, tetrachloroethane, carbon tetrachloride, trichloroethane, trichloroethylene, pentachloroethane, cis-dichloroethylene, o-, m- and p-difluorobenzene, 1,2-dichloroethane, 1,1-dichloroethane, n-propyl chloride, 1,2-cis-dichloroethylene, n-butyl chloride, 2-, tert.- and isobutyl chloride, chlorobenzene, bromobenzene, iodobenzene, o-, p- and m-dichlorobenzene, fluorobenzene, o-, p- and m-dibromobenzene, o-, m- and p-chlorotoluene, 1,2,4-trichlorobenzene, 1,10-dibromodecane, amyl chloride, cyclohexyl chloride, 1,3-dichloropropane, 1,4-dichlorobutane, isopropyl bromide, n-propyl bromide, butyl bromide, ethyl iodide, propyl iodide, chloronaphthalene, dichloronaphthalene and 1,4-dibromobutane, ethers, eg. n-butyl ethyl ether, ethyl propyl ether, methyl tert.-butyl ether, di-n-butyl ether, di-iso-amyl ether, di-iso-propyl ether, anisole, phenetole, cyclohexyl methyl ether, tetrahydrofuran, thioanisole and $\beta, \beta'$-dichlorodiethyl ether, ketones, eg. methyl ethyl ketone, diethyl ketone, acetophenone and cyclohexanone, esters, eg. methyl acetate, methyl benzoate, methyl propionate, butyl acetate, ethyl formate, ethyl acetate, methyl phthalate and phenyl acetate, nitrohydrocarbons, eg. nitromethane, nitroethane, nitrobenzene, o-, m- and p-chloronitrobenzene and o-nitrotoluene, nitriles, eg. acetonitrile, benzonitrile and m-chlorobenzonitrile, aliphatic or cycloaliphatic hydrocarbons, eg. decane, dodecane, hexane, heptane, nonane, gasoline fractions, cyclohexane, methylcyclohexane, cyclooctane, cyclododecane, petroleum ether, decalin, ligroin, 2,2,4-trimethylpentane, 2,2,3-trimethylpentane, 2,3,3-trimethylpentane and octane, and appropriate mixtures.

Suitable amounts of solvent to be used are from 50 to 3,000 percent by weight, preferably from 80 to 900 percent by weight, based on starting material II (carbamic acid halide).

Suitable gases which are inert under the reaction conditions are the rare gases, eg. xenon, argon, neon and helium, alkanes, eg. methane, ethane, propane, 2,2-dimethylpropane, butane, pentane and isobutane, gaseous halohydrocarbons, eg. tetrafluoromethane, dichloromethane, chloromethane, bromomethane, hexafluoroethane, chloroethane and fluoroethane, gaseous organometallic compounds, eg. tetramethylsilane, ethers, eg. dimethyl ether and methyl ethyl ether and, preferably, nitrogen, oxygen, air and/or carbon dioxide, and appropriate mixtures.

In a preferred embodiment of the process, at least 80, preferably from 150 to 10,000, and especially from 200 to 8,000 parts by volume of inert gas per part by volume of carbamic acid halide (starting material II) are employed, and advantageously the amount of solvent used, based on starting material II, is that indicated above. The preferred flow rate of the inert gas through the decomposition mixture is from 10 to 300, especially from 30 to 240, parts by volume per hour per part of starting material II.

An isocyanate-containing solution which is advantageously taken from the first and/or the second reaction vessel is used to free the inert gas from hydrogen halide.

The recombination of hydrogen halide with isocyanate to give carbamic acid halide takes place at below the decomposition temperature, preferably at from −30° to +40° C.

The process according to the invention can be carried out batchwise or, preferably, continuously, under atmospheric and/or superatmospheric pressure, but advantageously, in the first stage, under atmospheric pressure and, in the second stage, under the pressure which is essentially determined by the resistance presented to the inert gas flow by the reaction mixture in the second reaction vessel and the inert gas washing fluid in the particular apparatus employed.

The decomposition of the carbamic acid halides II can also be carried out in more than two stages, the additional stages being subsidiary stages of the first and second of the stages which have been described.

The isocyanates which can be prepared by the process of the invention, preferably ethyl isocyanate, n-propyl isocyanate and isopropyl isocyanate, are valuable starting materials for the manufacture of plant protection agents, pesticides, dyes, synthetic resins and plastics, textile waterproofing agents, detergents, bleaching agents and adhesives. In particular, their ability to produce conversion to urethanes, eg. for use as foams or high molecular weight coatings of high flexibility, and their conversion to ureas, are of importance. Details of their uses may be found in the above publications and in Ullmanns Encyklopadie der technischen Chemie, Volume 9, 3rd Edition (1957), pages 11, 12 and 404, and Volume 17, 3rd Edition (1966), page 204.

An apparatus suitable for continuous operation is shown in the FIGURE.

Its essential parts comprise the stock vessel 3 for the mixture of carbamic acid halide and solvent; the reaction vessel 1 (liquid capacity 2,500 parts by volume), the contents of which are heated to the reflux temperature, and which is equipped with a stirrer 4, and surmounted by a feed receiver 5 for the mixture of alkylcarbamic acid halide and solvent and a reflux condenser 6 through which all the hydrogen halide escapes, with a reflux overflow receiver from which part of the reflux condensate returns into the reaction vessel 1; a cooler 7, through which another portion of the material in the reflux overflow receiver is pumped (by means of pump 8) and is cooled at the same time; an insulated absorption column 9, filled with Raschig rings, to which this cooled liquid from the reflux overflow receiver is returned, the material leaving the column flowing back into the reaction vessel 1; the reaction vessel 2 (liquid capacity 2,200 parts by volume), the contents of which are heated to the reflux temperature, and which is equipped with a stirrer 10, means of introducing material from the reaction vessel 1, and inert gas inlet 11 and a reflux condenser 12, through which the inert gas, laden with hydrogen halide, is fed to the absorption column 9, in co-current with the cooled liquid from the reflux overflow receiver; a blower 13 which returns the inert gas, which has been freed from hydrogen halide in the absorption column, into the reaction vessel 2; the cooler 14 and a receiver 15 for the solution, containing isocyanate, which leaves the reaction vessel 2.

By way of example, the decomposition can be carried out as follows, in accordance with the FIGURE:

The starting material II, mixed with the solvent or separate therefrom, is fed continuously to the reaction vessel 1, whilst stirring. The contents of the reaction vessel are heated to the reflux temperature. All the hydrogen halide escapes through the reflux condenser 6. Any isocyanate, carbamic acid haide and/or solvent entrained through the condenser by the hydrogen halide can, eg., be washed out with solvent and returned to the reaction vessel 1. The hydrogen halide discharged can be absorbed in water to give the hydrohalic acid. From the reaction vessel 1, the solution, in which the alkylcarbamic acid halide has been substantially decomposed to alkyl isocyanate, flows into the reaction vessel 2, which is also heated to the reflux temperature, at a rate equal to the feed into the reaction vessel 1. Inert gas is passed through the mixture in reaction vessel 2. This gas, together with the hydrogen halide eliminated in the reaction vessel 2, escapes through the reflux condenser 12 and is fed to the absorption column in counter-current or, as in the case shown in the FIGURE, in co-current with the absorption solution. This absorption solution originates from reaction vessel 1 and/or 2 or, as shown in the FIGURE, from a reflux overflow receiver of the condenser 6 and/or a reflux overflow receiver, not shown in the FIGURE, of the condenser 12. In each case, the absorption liquid is cooled before being fed to the absorption column. The amount of absorption liquid fed into the column is at least sufficient that the hydrogen halide originating from reaction vessel 2 is completely bonded chemically by the isocyanate in the absorption liquid at the temperature in the column. The absorption liquid, enriched with carbamic acid halide, runs off into the reaction vessel 1, whilst the inert gas which is now free from hydrogen halide is returned to the reaction vessel 2, eg. by means of a blower, if necessary after passing through a cooler. The carbamic acid halide solution decomposed to isocyanate in the reaction vessel 2 can run into a collecting vessel through the cooler 14 and can be employed, as obtained, for further chemical reactions, or be subjected to fractional distillation to isolate the isocyanate.

Examples of the process, for the manufacture of ethyl isocyanate, n-propyl isocyanate and i-propyl isocyanate, are to be found in the Table which follows, and relate to the FIGURE.

The measurements shown in the Table were obtained with the apparatus operating continuously.

TABLE

| R in RNHCOCl | Solvent | C₁ concentration of RNHCOCl in % by weight | X measurement after x hours' operating time | C₂/C₃ ratio of RNHCOCl/RNCO in % by weight (see drawing) | C₄/C₅ ratio of RNHCOCl/RNCO in % by weight (see drawing) | $a_1/a_2$ HCl/RNHCOCl in % by volume, composition determined by gas analysis (see drawing) | $a_3/a_4$ HCl/RNHCOCl in % by volume, composition determined by gas analysis (see drawing) | $f_1$ feed in parts by volume per hour | $f_2$ amount of inert gas in parts by volume per hour | yield of distilled RNCO based on RNHCOCl employed | Boiling point |
|---|---|---|---|---|---|---|---|---|---|---|---|
| i-C₃H₇ | Toluene | 26.3 | 46.5 | 2/18.2 | —/21 | 2.1/<5×10⁻² | <0.1/<5×10⁻² | 500 | 50,000 (N₂) | 98% | 74° C |
|  |  |  | 47.5 | 3/19 | —/20.6 | 3.0/<5×10⁻² | <0.1/<5×10⁻² | 500 | 50,000 (N₂) |  |  |
|  |  |  | 48.5 | 3/18 | —/19 | 3.5/<5×10⁻² | <0.1/<5×10⁻² | 500 | 50,000 (N₂) |  |  |
|  |  |  | 49.5 | 4-5/26 | <0.1/23 | 2.7/<5×10⁻² | <0.1/<5×10⁻² | 500 | 50,000 (N₂) |  |  |
|  |  |  | 50.5 | 4/27 | <0.1/24 |  |  | 500 | 50,000 (N₂) |  |  |
| n-C₃H₇ | Chlorobenzene | 32.3 | 32 | 4/27 | 0.2/14 | 1.2/<5×10⁻² | <0.1/<5×10⁻² | 400 | 70,000 (CO₂) | 96% | 88° C |
|  |  |  | 33 | 2.5/17 |  | 1.9/<5×10⁻² | <0.1/<5×10⁻² | 400 | 70,000 (CO₂) |  |  |
|  |  |  | 34 |  |  |  |  | 400 | 70,000 (CO₂) |  |  |
|  |  |  | 35 |  |  |  |  | 400 | 70,000 (CO₂) |  |  |
|  |  |  | 36 |  |  |  |  |  |  |  |  |
| C₂H₅ | Methylcyclohexane | 21 | 35 | 3/17 | 0.3/12 | 1.3/<5×10⁻² | <0.1/<5×10⁻² | 300 | 60,000 (N₂) | 95% | 59.5–60.5° C |
|  |  |  | 36 | 2/18 | 0.2/13 |  |  | 300 | 60,000 (N₂) |  |  |
|  |  |  | 37 |  |  |  |  | 300 | 60,000 (N₂) |  |  |
|  |  |  | 38 |  |  |  |  | 300 | 60,000 (N₂) |  |  |
|  |  |  | 39 |  |  |  |  |  |  |  |  |

I claim:

1. A process for the manufacture of an aliphatic isocyanate of the formula $$R-N=C=O \qquad \text{I}$$

where R is an aliphatic radical of 1 to 10 carbon atoms, by thermal decomposition of an aliphatic carbamic acid halide of the formula

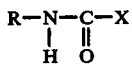

$$\qquad \text{II}$$

where R has the above meaning and X is halogen, in the presence of an inert organic solvent, wherein the thermal decomposition is carried out in the presence of the inert organic solvent in a first reaction vessel for not longer than is required to set up the equilibrium of the thermal decomposition reaction, the hydrogen halide eliminated during this stage is removed through a reflux condenser, the carbamic acid halide/isocyanate mixture obtained in the first reaction vessel is transferred into a second reaction vessel, the thermal decomposition of the remaining carbamic acid halide is continued therein whilst passing inert gas through the mixture, the hydrogen halide entrained with the inert gas which is discharged from the second vessel is reacted with isocyanate at a temperature below the decomposition temperature by passing the hydrogen halide and inert gas in contact with an isocyanate of the formula I, thereby producing carbamic acid halide and purifying the inert gas of hydrogen halide, the mixture containing carbamic acid halide thus obtained is introduced into the first reaction vessel and the purified inert gas is recycled to the second reaction vessel.

2. A process as claimed in claim 1, wherein the decomposition is carried out at from 30° to 180° C.

3. A process as claimed in claim 1, wherein the decomposition is carried out with not less than 80 parts by volume of inert gas per part of carbamic acid halide.

4. A process as claimed in claim 1, wherein the inert organic solvent has a boiling point of not less than 60° C.

5. A process as claimed in claim 1 wherein part of the condensate of said reflux condenser is collected, cooled, and then supplied as said isocyanate of said formula I for said isocyanate-hydrogen halide reaction.

6. A process as claimed in claim 1, wherein the isocyanate of the formula I for said isocyanate-hydrogen halide reaction is a component of a mixture of said inert organic solvent and the carbamic acid halide/isocyanate mixture originating in the first and/or second reaction vessel.

7. A process as claimed in claim 1 wherein said isocyanate-hydrogen halide reaction is conducted at a temperature in the range of −30° to +40° C.

* * * * *